United States Patent [19]

Daniel

[11] Patent Number: 4,515,590
[45] Date of Patent: May 7, 1985

[54] AUTOMATIC INJECTION APPARATUS

[75] Inventor: Nisim Daniel, Kiriat Tivon, Israel

[73] Assignee: Abic Ltd., Israel

[21] Appl. No.: 463,559

[22] Filed: Feb. 3, 1983

[30] Foreign Application Priority Data

Feb. 16, 1982 [IL] Israel .................................... 65031

[51] Int. Cl.³ .............................................. A61M 5/00
[52] U.S. Cl. .................................... 604/144; 604/156
[58] Field of Search ............... 604/143, 144, 145, 147, 604/156

[56] References Cited

U.S. PATENT DOCUMENTS 3,768,472  10/1973  Hodosh et al. ................... 604/143
4,108,176   8/1978  Walden .............................. 604/147
4,177,810  12/1979  Gourlandt ........................ 604/144

*Primary Examiner*—John D. Yasko
*Attorney, Agent, or Firm*—Steinberg & Raskin

[57] ABSTRACT

The present invention relates to an automatic injection apparatus for animals, in particular for chicks, which comprises a housing, a syringe with an injection needle giving the injection through an aperture on the front wall of said housing, a two-way air double action piston being connected to said syringe and to a source of air, activating means for said piston and means for connecting the syringe to a liquid container. Said apparatus has optionally additional parts, e.g. a timer fixing the length of the period of the injection; an air regulator; means for cleaning the air; counters measuring the numbers of animals being injected and/or pre-setting the number of animals to be injected; and a disinfecting device for the needle.

17 Claims, 12 Drawing Figures

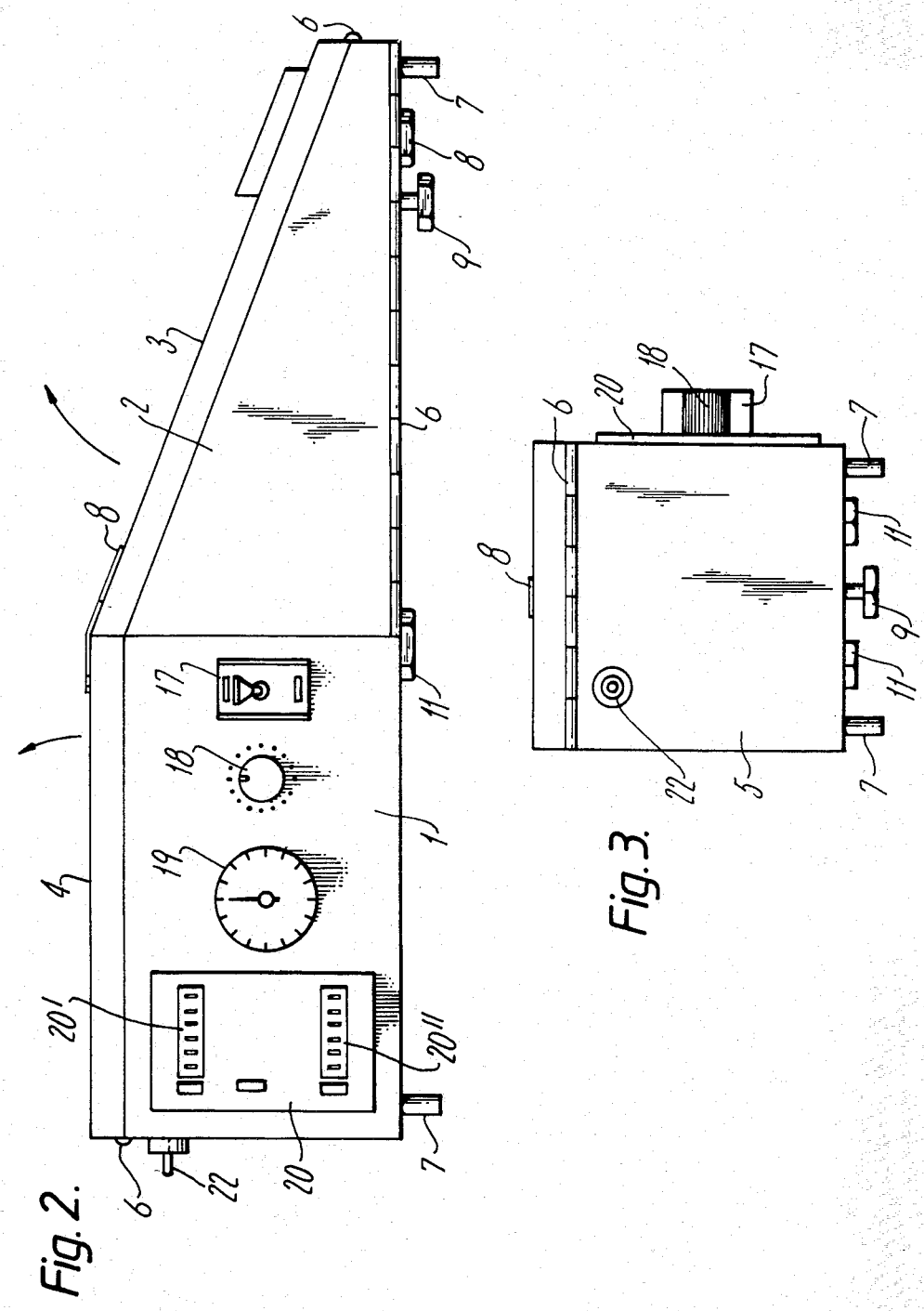

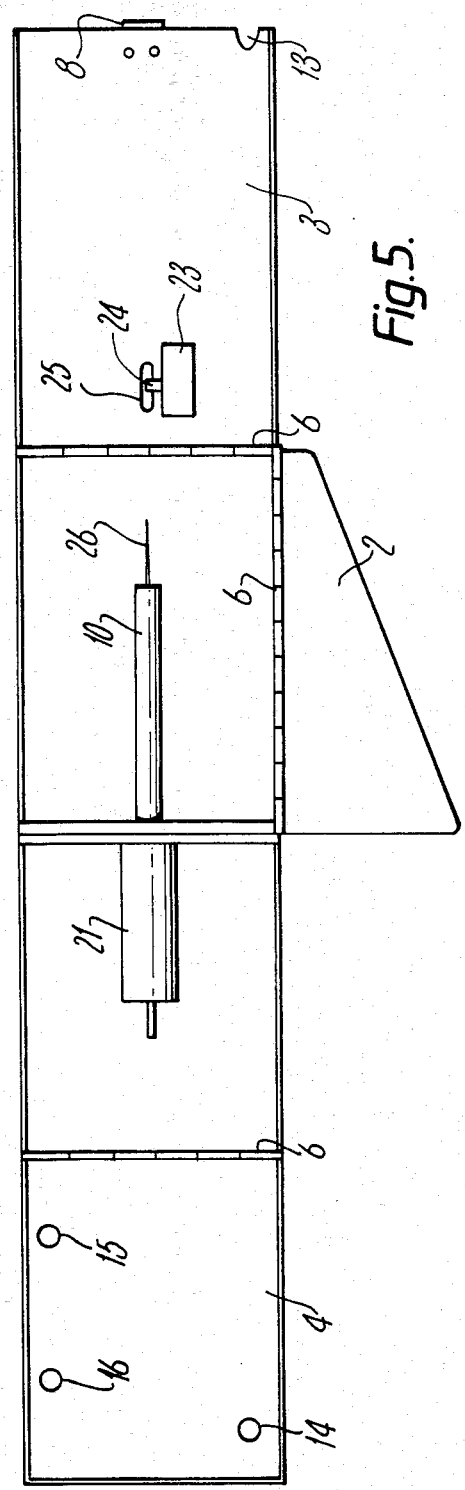
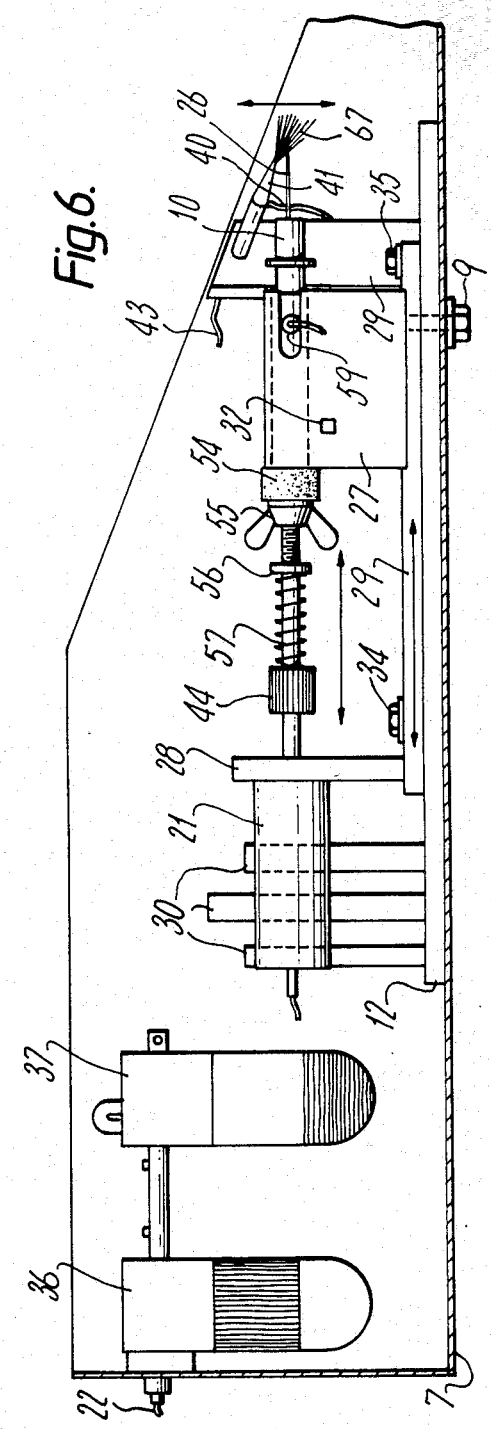

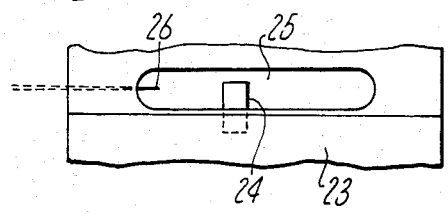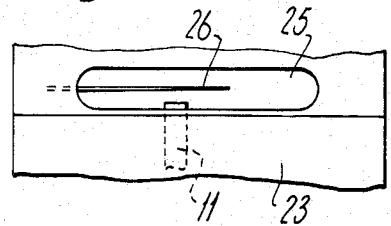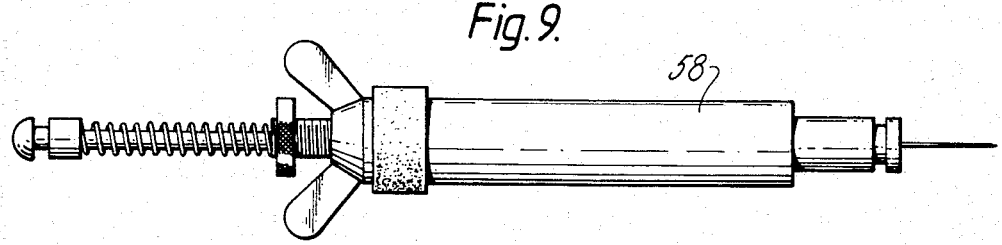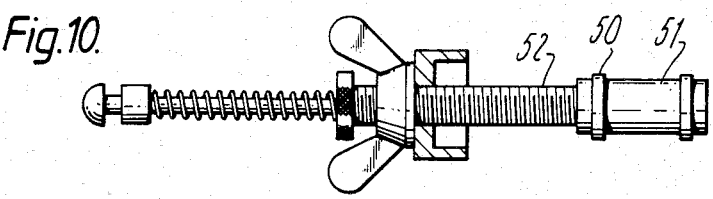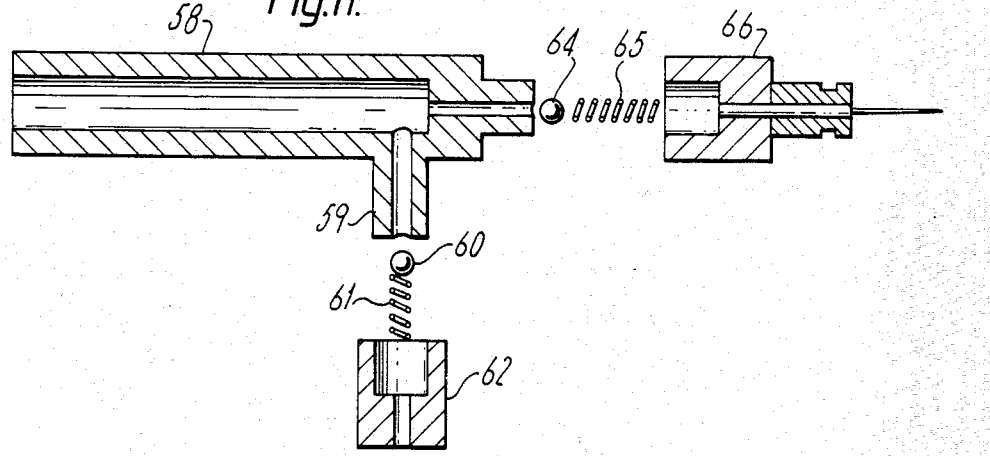

AUTOMATIC INJECTION APPARATUS

BACKGROUND OF THE INVENTION

The present invention relates to an automatic injection apparatus for animals, in particular chicks.

Chicks have to be vaccinated a few days after birth. The vaccination operation, which is preferred by way of injection, should be a quick one enabling in a relatively short time to vaccinate a large number of chicks, without requiring much man power and expensive apparatus.

There are known injection apparatus for this purpose, e.g., those described and claimed in U.S. Pat. Nos. 3,964,481, 4,108,176 and 4,276,879. Said devices comprise mainly a work plate on which the animal to be injected is placed, said plate being provided with an aperture through which a syringe needle may protrude to inject the animal, a syringe which is mounted on the side on which the animal is to be injected, first means for moving said syringe back and forth between a first position in which the syringe needle is entirely withdrawn and a second position in which said syringe needle protrudes through said aperture as well as means activating at the required moment said first means.

However, said known apparatus have certain drawbacks. Thus in the device of U.S. Pat. Nos. 3,964,481 and 4,276,879, as first means an electric motor is utilized. This has serious drawbacks in that such motors cause safety problems, in particular in wet hatcheries. Moreover, this apparatus although it is portable can be utilized only in the vicinity of a source of a wall current. Said electric motor is replaced in the apparatus of U.S. Pat. No. 4,108,176 by a piston (fluid motor). However, this apparatus has the drawback that said piston works in one direction only and is retracted by the force of a spring. This spring very often breaks and has then to be replaced in a rather complicated manner. Moreover, in such apparatus the syringe cannot be mounted on a support in a tight manner as this may also cause the breaking of the spring. Thus the syringe cannot be fixed on said support in a precise manner.

Moreover, most of the known apparatus have the common drawback that they are arranged in a closed housing, which can be opened only by complicated means. This brings about the replacement of parts, e.g., the above mentioned spring and/or the cleaning of the several parts becomes quite a complicated operation.

SUMMARY OF THE INVENTION

It has therefore been desirable to design an automatic injection apparatus of the above kind which overcomes the above drawbacks to a large extent. Said apparatus should be simple in its construction and in its use.

The present invention thus consists in an automatic injection apparatus comprising:

a. a housing formed by a plurality of walls the front oblique wall being the work plate on which the animal to be injected is placed, said wall being provided with an aperture through which an injection needle can protrude;

b. a syringe with an injection needle mounted in a tight manner on a support within said housing on the other side of the aperture of said working wall;

c. a two-way air double action piston suitably connected to said syringe and causing a forward and backward movement thereof;

d. means for connecting the piston to a source of air;

e. means for activating said piston in both directions; and f. means connecting the syringe to a container of the liquid to be injected.

As indicated above it is often important that one should have an easy access to the inside of the housing. Thus in a preferred embodiment of the present invention some of the walls open outwards on hinges, and in the closed position are held together by a suitable closing device, e.g. a catch. This embodiment enables easy access to all parts of the apparatus for cleaning and/or repair purposes.

In most of the known apparatuses the period during which the needle is within the animal to be injected cannot be precisely pre-determined. Thus, in a preferred embodiment of the present invention a timer is present, which timer sets the period between the beginning of the injection and the end thereof, i.e., the moment the piston moves backwards. This arrangement enables the use of viscous liquids and the injection of more mature animals.

Advantageously the apparatus according to the present invention is provided with an air regulator which ascertains that the air is provided always under the desired pressure, e.g., 5 atm. The air is supplied from any suitable source, e.g., an air compressor, bottles of compressed air, etc.

The air forwarded to the apparatus should be as clean as possible. Therefore advantageously in the air supply line an air filter and an air lubricator are positioned. This arrangement ascertains that the air reaching the piston is clean.

Moreover, the apparatus according to the present invention is preferably also provided with two counters, i.e., one measuring the total number of animals injected and the other by which the number of animals to be injected may be pre-set. This is often desirable as one then, for example, always injects the exact number of chicks to be packed in a box.

The injection liquid may be stored in any suitable container and forwarded to the syringe. Preferably two containers connected to each other are utilized thus ascertaining that there is always liquid present in the second container while the first one is being replaced. This arrangement has the additional advantage that the dirt which sometimes enters the supply hose is retained in the second container and therefore no dirt can clog the syringe.

The syringe and in particular the injection needle have to be disinfected at certain intervals, i.e., after a certain number of injections has been performed. Therefore advantageously the apparatus according to the present invention is also provided with a disinfecting device which comprises a container connected by suitable means to a sprayer and to actuating means. Said device may be actuated in several manners. In a preferred embodiment it is connected to the counter, if present, which determines the number of animals to be injected. Thus each time after a certain number of injections has been performed the disinfecting apparatus is actuated and the needle is disinfected. However, said disinfecting apparatus may be an entirely separate unit having its own actuating means being connected to the source of air.

In a preferred embodiment of the apparatus according to the present invention means are provided for fixing the needle at the desired angle and at the required distance from the animal. This enables also not only the injection of new born chicks by the apparatus according to the present invention but of more mature animals.

The support on which the syringe is mounted is advantageously provided with a groove on which the syringe can move. Moreover, it is provided with a screw which enables tightening of said groove.

The apparatus according to the present invention is preferably provided with means by which the piston and the syringe may be connected and disconnected quickly.

As actuating means a micro-switch is preferably utilized, which actuates the actual injection operation. Said micro-switch is preferably connected to a main switch which opens and closes the apparatus.

The entire apparatus is made from any suitable material. Thus most of the parts are made of stainless steel. The containers are preferably made of a plastic material. The support is advantageously made of hard and flexible plastic material (Oblon).

The syringe utilized in the apparatus according to the present invention may be any suitable, commercially available syringe. However, said syringes have certain drawbacks, inter alia, the following:

a. the volume of the injection liquid cannot be adjusted in the commercially available syringes hence one has always to inject the same dose of vaccinating material. This does not permit the use of the same syringe to inject new born chicks as well as more mature animals;

b. in the main body there is a free moving part wherefore the syringe is not tightly closed;

c. in the commercially available syringes one-way valves having rubber discs are utilized. These valves have the drawback that they cannot be heated. Moreover, they cause reduction of the volume in the course of the operation and/or cleaning.

The present invention thus also comprises a syringe comprising:

a. a rod bearing a spring, adjustment means and closing means, the front part of said rod entering into b. a hollow housing comprising an inlet for the liquid being connected to the supply line via a one-way valve; and, c. a hollow front housing comprising an injection needle being connected to said hollow housing via a one-way valve.

Said one-way valve is advantageously constituted by a ball valve.

The syringe may be so adjusted that the volume of the injection liquid is up to about 1.25 cc.

The invention is described herein with reference to vaccinating chicks and more mature animals. However, it is readily understood that the invention is not restricted to this use. The apparatus may be utilised for administering injections for any suitable purpose to any animal of appropriate size.

BRIEF DESCRIPTION OF THE DRAWINGS

The present invention will now be illustrated with reference to the accompanying drawings without being limited by same. In said drawings:

FIG. 2 shows a side view of the apparatus shown in FIG. 1;

FIG. 3 shows a back view of the apparatus shown in FIG. 1;

FIG. 5 shows a schematical top view of the apparatus shown in FIG. 1 in open position;

FIG. 6 shows a section along line VI—VI in FIG. 1;

FIGS. 8' and 8" show in detail the position of the syringe needle is withdrawn and in injecting position, respectively;

FIG. 9 shows a top view of a syringe according to the present invention without the rod part;

FIG. 10 shows the rod part of the syringe according to the present invention; and FIG. 11 shows a partial side section of the part of the syringe shown in FIG. 9.

DETAILED DESCRIPTION OF THE PREFERRED EMBODIMENT

Figure 1:
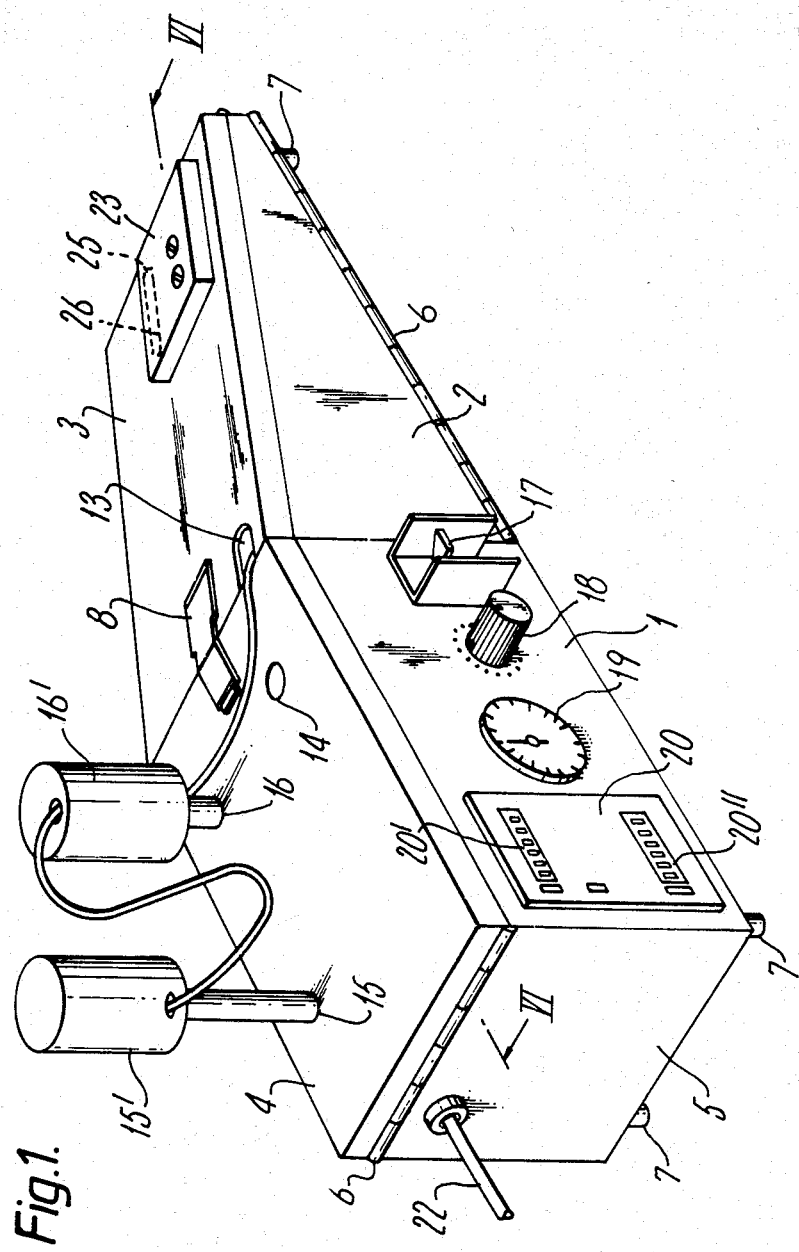
FIG. 1 shows a perspective view of a closed apparatus according to the present invention.
Figure 4:
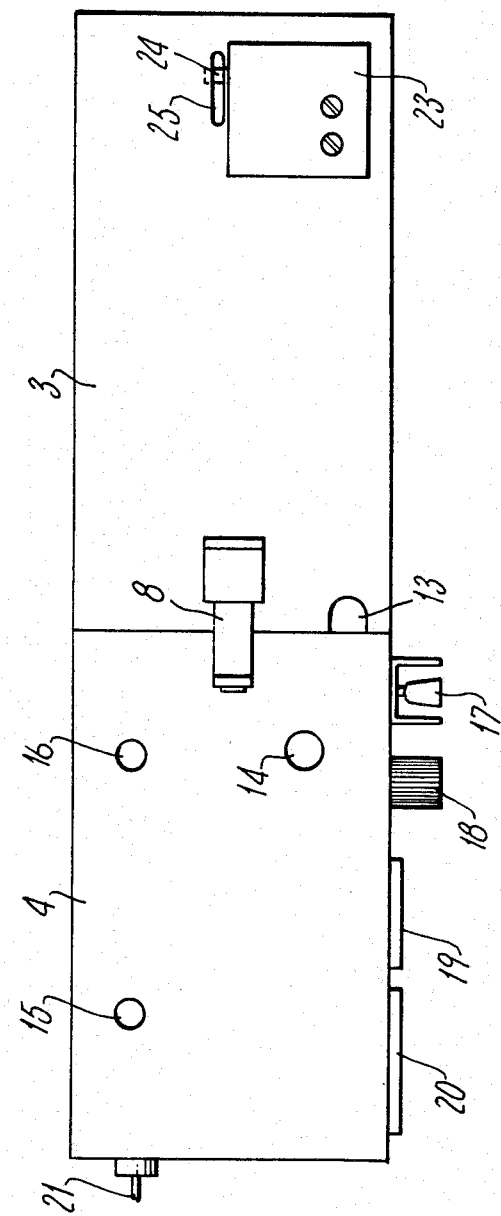
FIG. 4 shows a top view of the apparatus shown in FIG. 1.
Figure 7:
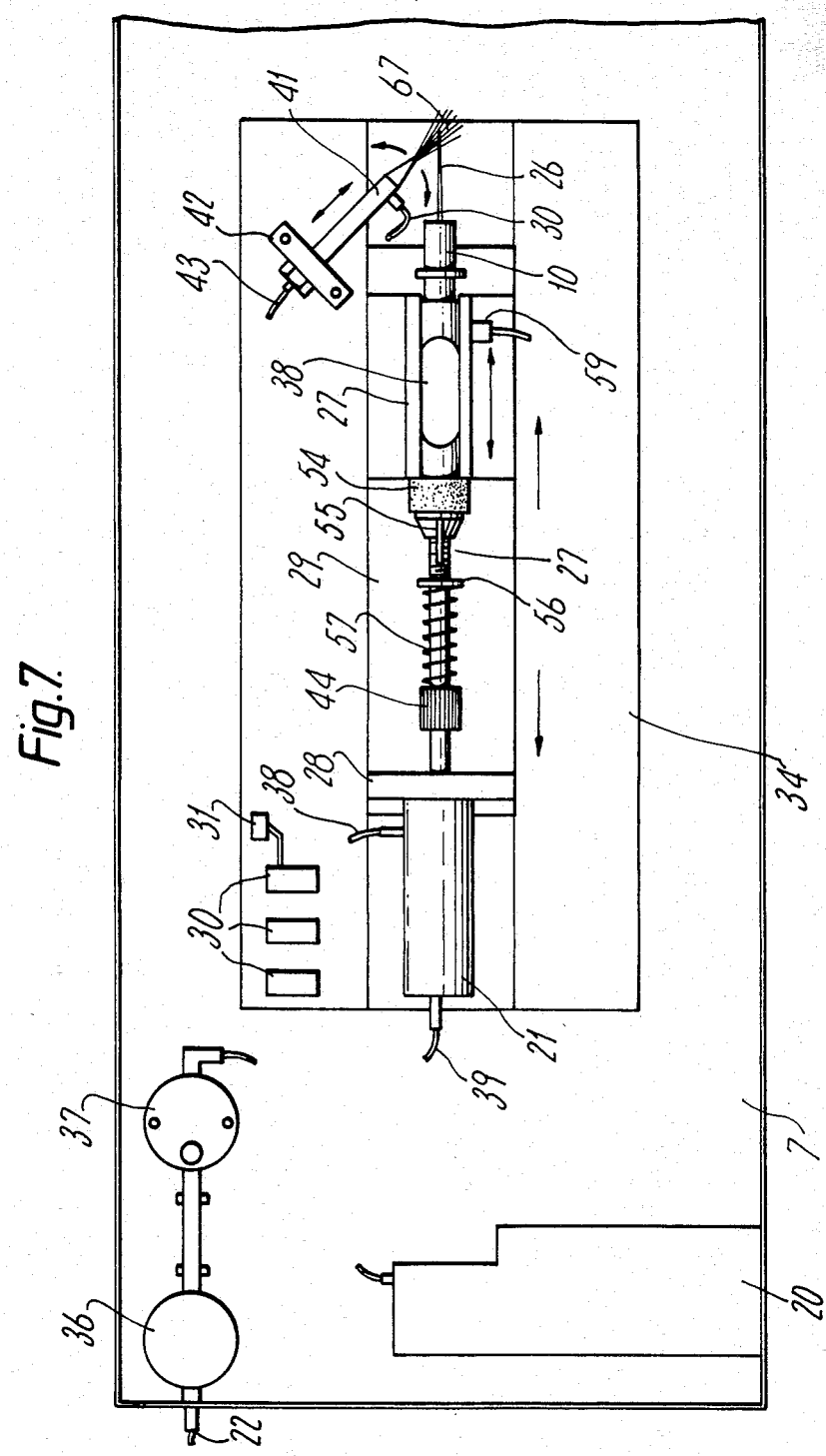
FIG. 7 shows in detail a top view of the apparatus shown in FIG. 1 without the openable walls.

The apparatus illustrated in FIGS. 1 to 8 comprises a housing constituted by wall 1 and a parallel wall thereto (not shown), oblique openable wall 2 and a parallel wall thereto (not shown), openable front wall 3, openable top plate; back wall 5 and bottom plate 7 standing on feet 7'. Openable walls 2, 3 and 4 rotate on hinges 6.

Walls 2 and 3 and roof plate 4 are held together by catch 8 which can be opened easily.

Below bottom plate 7 are arranged adjustment screw 9 which adjusts the height of syringe 10, and screws 11 for connecting plate 7 to plate 12.

There are arranged bores 13 (on plate 3) and 14 (on plate 4). On plate 4 are placed supports 15 and 16 carrying containers 15' and 16' respectively. Said containers 15' and 16' are for the vaccinating liquid. Container 15' is the main one and container 16' the second one which is always full when container 15' is replaced. The liquid is supplied to syringe 10 through a hose (not shown) via hole 13. Advantageously mounted on hole 14 is a measuring device (not shown) for measuring the liquid used.

On wall 1 are fixed actuating device 17, air regulator 18 which is connected to air pressure measuring device 19 and counters 20. Counter 20' counts the entire amount of injections administered and counter 20" enables to pre-determined the number of injections to be administered.

Air required for actuating piston 21 is introduced through hose 22, passing through wall 5.

On wall 3 are arranged housing 23 of microswitch 24, and aperture 25 through which needle 26 can protrude and perform the injection. Housing 23 can be moved on plate 3 to the left or right by way of screws (not shown). This arrangement enables the fixing of the distance from aperture 25 in accordance with the size of the animal to be injected.

Syringe 10 is mounted on plastic support 27 which is mounted together with base 28 of piston 21 on plate 29. Said plate 29 is mounted together with valves 30 and timer 31 on plate 12 which in turn is connected by screws 11 to plate 7.

Screw 32 is placed on support 27. Said screw 32 tightens syringe 10 within groove 33.

Plate 29 is fixed to plate 12 by way of screws 34 and 35 which are arranged in small grooves (not shown). By placing said screws 34 and 35 in the proper place the required distance from syringe 10 to wall 3 may be determined. The required angle of syring 10 within aperture 25 is adjusted by screw 9 which raises and lowers support 27.

The apparatus illustrated in FIGS. 1 to 8 comprises also a disinfecting device which comprises a container (not shown) connected to inlet 40 of sprayer 41 which sprayer 41 is a venturi nozzle. Nozzle 41 is mounted on base 42 which is provided with air inlet 43.

Syringe 10 is connected to piston 21 by connecting screw 44. Thus syringe 10 can be easily removed and replaced.

Syringe 10 utilized in the apparatus illustrated in FIGS. 1 to 8 is shown in detail in FIGS. 9 to 11.

Said syringe comprises rod 50 having front part 51. There is provided spring 52 on which sit discs 53, closing screw 54, closing nut 55, adjustment nut 56 and spring 57.

Front part 51 is inserted into body 58 being provided with inlet 59 which is connected via ball 60 and spring 61 to part 62. Inlet 59 and part 62 are screwed together. The injection liquid is provided from container 16 to part 62.

At the front, body 58 is connected via ball 64 and spring 65 by way of screwing to body 66 bearing at the front injection needle 26.

The apparatus illustrated herein operates as follows:

Syringe 10 is fixed in the desired position and at the desired angle by screws 34 and 35; and 9 respectively. Housing 23 is also fixed in the desired position. Moreover the desired volume of liquid to be injected is fixed by adjustment nut 56. Thereafter syringe 10 is closed by screw 54.

The required air pressure is chosen by air regulator 18. Counter 20'' is fixed, if desired, to a certain number of injections. The disinfecting apparatus is optionally also connected to counter 20'' ascertaining that needle 26 is disinfected at pre-determined intervals.

Vaccinating liquid is put into containers 15' and 16'. The housing is brought into the closed position. The apparatus is thus ready for operation and actuating device 17 is put in operation position. The chick to be injected is put in injection position on plate 3. The operator presses microswitch 24 which brings about the introduction of air into piston 21 via opening 38. Piston 21 moves forward pressing syringe 10 forward, until discs 53 hit support 27. Spring 57 presses rod 50 forwards and thus causes the required amount of liquid to flow via inlet 59 to injection needle 26 which protrudes through aperture 25 performing the injection.

When the injection has been performed—i.e., after the time fixed by timer 31 has lapsed, air is introduced into piston 21 via opening 38 causing piston 21 to move backwards drawing syringe 10 together therewith.

This cycle is repeated until the number of chicks fixed by counter 20'' has been injected. In case that the disinfecting device is actuated by counter 20'', the disinfecting liquid is sprayed by venturi nozzle 41 as spray 67. Thereafter actuating device 17 moves into closed position.

When a new batch is to be injected actuating device 17 is again put on and the entire operation is repeated.

The moment container 15' is empty it is refilled or replaced without the operation being interrupted as liquid is still present in container 16'.

When the various parts of the apparatus have to be cleaned and/or replaced catch 8 is released, walls 2, 3 and 4 open outwards and one has easy access to all parts, enabling the desired operation to be performed.

I claim:

1. An automatic injection apparatus, comprising a housing formed by a plurality of walls, one of said walls extending obliquely and constituting an injection wall,
a aperture formed in said injection wall,
a syringe disposed within said housing,
an injection needle disposed on one end of said syringe,
a support disposed within said housing upon which said syringe is tightly mounted and adapted to slide therealong, so that said needle protrudes through said aperture,
means for introducing injection fluid into said syringe,
a two-way, fluid-actuated, double action piston coupled to said syringe for moving the latter in both a forward and a backward direction along said support,
means for fluidly connecting said piston to a source of fluid under pressure, said fluid connecting means including
means for introducing pressurized fluid on one side of said piston, to cause the same and said syringe to move in the forward direction, and
means for introducing pressurized fluid on another side of said piston to cause the same and said syringe to move in the backward direction.

2. An injection apparatus according to claim 1, in which some of the walls open outwards being kept in the closed position by a catch.

3. Injection apparatus according to claim 1, which comprises a timer setting the period between the beginning of the injection and the end thereof.

4. Injection apparatus according to claim 1 which comprises an air regulator.

5. Injection apparatus according to claim 1 which comprises an air filter and an air lubricator.

6. Injection apparatus according to claim 1 which comprises two counters, one measuring the total number of animals injected and the other by which the number of animals to be injected may be pre-set.

7. Injection apparatus according to claim 1, in which said means for introducing injection fluid comprises two containers for the injection fluid suitably connected to each other.

8. Injection apparatus according to claim 1 which comprises a disinfecting device which comprises a container connected by suitable means to a sprayer and to actuating means.

9. Injection apparatus according to claim 1 which comprises means for fixing the needle at the desired angle and at the required distance from the animal to be injected.

10. Injection apparatus according to claim 1 in which said support is provided with a groove for the syringe and with means for fixing the syringe tightly within said groove.

11. Injection apparatus according to claim 1 wherein said actuating means is a micro-switch being connected to a main switch.

12. Injection apparatus according to claim 1 which comprises a syringe, comprising:
a. a rod bearing a spring, adjustment means and closing means, the front part of said rod entering into
b. a hollow housing comprising an inlet for the injection fluid being connected to the means for introducing injection fluid via a one-way valve; and,
c. a hollow front housing comprising an injection needle being connected to said hollow housing via a one-way valve.

13. Injection apparatus according to claim 12, in which both said one-way valves are a ball valve.

14. An automatic injection apparatus, comprising
a housing formed by a plurality of walls,
one of said walls extending obliquely and constituting an injection wall,
an aperture formed in said injection wall,
a syringe disposed within said housing and comprising
a hollow body portion,
an injection needle connected to said hollow body portion,
means for introducing injection fluid into said hollow body portion,
a rod extending into said hollow body portion to define a space therewithin for a finite quantity of fluid to be injected,
first means for adjusting position and angle of said syringe within said housing,
second means for adjusting position of said rod within said hollow body portion to define the size of said space for receiving the injection fluid,
means for extending said rod into said hollow body portion to contract said space and expel injection fluid through said needle, and for retracting said rod out of said hollow body portion to return said rod to the adjusted position thereof,
a support disposed within said housing upon which said syringe is tightly mounted and adapted to slide therealong so that said needle protrudes through said aperture,
a two-way, fluid-actuated, double action piston coupled to said syringe for moving the latter in both a forward and a backward direction along said support, said piston engaged with said extending and retracting means,
means for stopping forward movement of said syringe with respect to said support,
means for fluidly connecting said piston to a source of fluid under pressure, said fluid connecting means including
means for introducing pressurized fluid on one side of said piston, to cause the same and said syringe to move in the forward direction, and
means for introducing pressurized fluid on another side of said piston, to cause the same in said syringe to move in the backward direction.

15. The apparatus of claim 14 wherein said second adjusting means comprises
a spring engaged with said rod and with said piston, and
a nut disposed adjacent said spring and adapted to be adjusted to tighten or loosen said spring, thereby adjusting position of said rod within said hollow body portion of said syringe to define the size of said space for receiving the injection fluid, and
said first adjusting means compriss
an adjustable plate disposed underneath said support and comprising a plurality of grooves,
a plurality of screws adapted to affix said plate to said housing through said grooves such that position of said plate is adjustable over the length of said grooves, and
a screw engaged with said support and adapted to adjust the height thereof, thereby adjusting angle of inclination of said syringe with respect to said aperture.

16. The apparatus of claim 15 wherein said syringe additionally comprises
a one-way valve disposed between said space containing the injection fluid and said needle, and
said means for introducing injection fluid into said syringe comprises
an inlet into said space, and p1 a one-way valve disposed within said inlet.

17. An automatic injection apparatus, comprising
a housing formed by a plurality of walls,
one of said walls extending obliquely and constituting an injection wall,
an aperture formed in said injection wall,
a syringe disposed within said housing,
an injection needle disposed on one end of said syringe,
a support disposed within said housing upon which said syringe is tightly mounted and adapted to slide therealong, so that said needle protrudes through said aperture,
means for introducing injection fluid into said syringe,
a two-way, fluid-actuated, double action piston coupled to said syringe for moving the latter in both a forward and a backward direction along said support,
means for fluidly connecting said piston to a source of fluid under pressure, said fluid connecting means including
means for introducing pressurized fluid on one side of said piston, to cause the same in said syringe to move in a forward direction, and
means for introducing pressurized fluid on another side of said piston to cause the same and said syringe to move in the backward direction,
means for disinfecting said needle comprising
a container for disinfecting fluid,
a sprayer disposed adjacent said needle, and
conduit means for connecting said container with said sprayer,
a fluid filter and lubricator disposed within said fluidly-connecting means,
means for fixing said injection needle at a desired angle and at a required distance from an animal to be injected, and
said syringe comprising
a hollow body portion connected to said needle at one end,
a rod extending into said hollow body portion to define a space therewithin for a finite quantity of fluid to be injected,
means for introducing injection fluid into said space comprising an inlet and a one-way valve disposed therewithin,
a one-way valve disposed between said space and said injection needle,
means for adjusting position of said rod within said hollow body portion, and
means for stopping forward movement of said syringe after a certain point.

* * * * *